United States Patent
Hoeg-Jensen et al.

(10) Patent No.: US 7,572,884 B2
(45) Date of Patent: Aug. 11, 2009

(54) METHOD FOR MAKING ACYLATED POLYPEPTIDES

(75) Inventors: Thomas Hoeg-Jensen, Klampenborg (DK); Michi Egel-Mitani, Vedbaek (DK); Per Balschmidt, Espergaerde (DK); Jan Markussen, Herlev (DK); Ivan Diers, Vaerlose (DK)

(73) Assignee: Novo Nordisk A/S, Bagsvaerd (DK)

( * ) Notice: Subject to any disclaimer, the term of this patent is extended or adjusted under 35 U.S.C. 154(b) by 281 days.

(21) Appl. No.: 11/191,574

(22) Filed: Jul. 28, 2005

(65) Prior Publication Data

US 2005/0272125 A1    Dec. 8, 2005

Related U.S. Application Data (63) Continuation of application No. 10/205,270, filed on Jul. 24, 2002, now abandoned.

(60) Provisional application No. 60/310,952, filed on Aug. 8, 2001.

(30) Foreign Application Priority Data

Jul. 24, 2001  (DK) .............................. 2001 01140

(51) Int. Cl.
*A61K 38/00* (2006.01)
*A61K 38/04* (2006.01)

(52) U.S. Cl. ................. 530/345; 530/330; 530/329; 530/324; 514/2; 514/12

(58) Field of Classification Search ............. 530/345
See application file for complete search history.

(56) References Cited

U.S. PATENT DOCUMENTS

| 5,252,466 A | 10/1993 | Cronan, Jr. ................ 435/69.7 |
| 5,316,923 A | 5/1994 | Christiansen .............. 435/69.9 |
| 5,646,242 A | 7/1997 | Baker et al. ................ 530/303 |
| 5,905,140 A | 5/1999 | Hansen ...................... 530/303 |
| 6,011,007 A | 1/2000 | Havelund et al. ............ 514/3 |

FOREIGN PATENT DOCUMENTS

| EP | 0712862 A2 | 5/1996 |
| WO | WO 95/35384 | 12/1995 |
| WO | WO 98/00872 | 3/1998 |
| WO | WO 98/08871 | 3/1998 |
| WO | WO 98/08872 | 3/1998 |
| WO | WO 00/55119 | 9/2000 |

*Primary Examiner*—Cecilia Tsang
*Assistant Examiner*—Maury Audet
(74) *Attorney, Agent, or Firm*—Shelby J. Walker (57) ABSTRACT

The present invention related to a method of producing polypeptides in transformed host cells by expressing a precursor molecule of the desired polypeptide which are to be acylated in a subsequent in vitro step. The invention is also related to DNA-sequences, vectors and transformed host cells for use in the claimed method. Further, the present invention is related to certain precursors of the desired polypeptides and certain acylation methods. The invention provides a method for making polypeptides being preferentially acylated in certain lysine $\epsilon$-amino groups.

6 Claims, 1 Drawing Sheet

Fig. 1

SEQUENCE LISTING

<160> NUMBER OF SEQ ID NOS: 16

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Glu Glu Ala Glu Met
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Glu Glu Ala Glu Asn
1               5

<210> SEQ ID NO 3
<211> LENGTH: 6
<212> TYPE: PRT

```
<213> ORGANISM: Artificial Sequence
<220> FEATURE:
<223> OTHER INFORMATION: Synthetic

<400> SEQUENCE: 3

Glu Glu Ala Glu Arg Arg
 1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic

<400> SEQUENCE: 4

Gln Glu Pro Gln
 1

<210> SEQ ID NO 5
<211> LENGTH: 5
<212> TYPE: PRT
<213> ORGANISM: Artificial Sequence
<220> FEATURE:
<223> OTHER INFORMATION: Synthetic

<400> SEQUENCE: 5

Glu Ala Glu Ala Gln
 1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Glu Ala Glu Ala Glu Ala Gln
 1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Glu Glu Gly Cys Thr Ser Ile Cys
 1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Glu His Gly Cys Thr Ser Ile Cys
 1               5

<210> SEQ ID NO 9
<211> LENGTH: 5
<212> TYPE: PRT
<213> ORGANISM: Artificial Sequence
```

```
<220> FEATURE:
<223> OTHER INFORMATION: Synthetic

<400> SEQUENCE: 9

Glu Glu Ala Arg Met
 1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic

<400> SEQUENCE: 10

Glu Glu Arg Asn
 1

<210> SEQ ID NO 11
<211> LENGTH: 5
<212> TYPE: PRT
<213> ORGANISM: Artificial Sequence
<220> FEATURE:
<223> OTHER INFORMATION: Synthetic

<400> SEQUENCE: 11

Glu Glu Ala Glu Asn
 1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Glu Glu Arg Ala Arg Arg
 1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic

<400> SEQUENCE: 13

Glu Glu Ala Glu Pro
 1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic

<400> SEQUENCE: 14

Glu Glu Gly Glu Pro
 1               5

<210> SEQ ID NO 15
<211> LENGTH: 5
<212> TYPE: PRT
<213> ORGANISM: Artificial Sequence
<220> FEATURE:
```

```
<223> OTHER INFORMATION: Synthetic

<400> SEQUENCE: 15

Glu Glu Ala Glu Cys
 1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic

<400> SEQUENCE: 16

Glu Glu Ile Glu Gly Arg
 1               5
```

METHOD FOR MAKING ACYLATED POLYPEPTIDES

CROSS REFERENCE TO RELATED APPLICATIONS

This application is a continuation of application Ser. No. 10/205,270 filed Jul. 24, 2002 now abandoned and claims priority under 35 U.S.C. 119 of Danish application no. PA 2001 01140 filed on Jul. 24, 2001 and of U.S. application No. 60/310,952 filed on Aug. 8, 2001, the contents of each of which are fully incorporated herein by reference.

FIELD OF THE INVENTION

The present invention is related to a method of producing acylated proteins or polypeptides by expressing certain precursors of the desired polypeptide that protects the expressed polypeptide against proteolytic degradation within the host cell. The invention is also related to DNA-sequences, vectors and transformed host cells for use in the claimed method. Furthermore, the present invention is related to certain precursors of the desired polypeptides and an acylation method for acylation method for acylation of one or more lysine residues in the desired polypeptide.

BACKGROUND OF THE INVENTION

Recombinant DNA technology has enabled expression of foreign (heterologous) polypeptides in microbial and other host cells. In yeast expression of heterologous polypeptides after transformation of yeast cells with suitable expression vectors comprising DNA sequences coding for said polypeptides has been successful for many species of polypeptides, such as insulin and insulin precursors, glucagon, glucagon like peptides and analogues thereof.

A common problem with expression of proteins or polypeptides of a limited size in a recombinant host is, however, proteolytic degradation of the expressed product by proteolytic enzymes produced by the host organism.

Thus, the isolated product may be a heterogeneous mixture of species of the desired polypeptide having different amino acid chain lengths. Another problem encountered in production of heterologous polypeptides in yeast may be low yield, presumably due to proteolytic processing both in intracellular compartments and at the plasma membrane caused by aberrant processing at internal sites in the polypeptide. Yeast contains a number of proteases used for processing yeast proteins e.g. Kex2p and Yps1p which cleave at the C-terminal side of a dibasic amino acid sequence, and the carboxypeptidase Kex1p which digests remaining basic amino acids after the endoproteolytic digestion by Kex2p, and Ste13p or Dap2p which cleave at X-Ala or X-Pro.

Some polypeptides, e.g. polypeptides having from about 10 to about 100 amino acids chains and none or a few disulphide bonds and/or are rich in basic amino acids, such as β-endorphine, glucagon and glucagon like peptides may be especially susceptible to intracellular and extracellular proteolytic degradation when expressed in a transformed host cell due to their short-chain open and non-disulfide stabilized structure resulting in an inhomogeneous product which may be proteolytically degraded in the N—and C-terminal ends as well as endoproteolytically degraded.

Furthermore, N-terminal cleavage of expressed polypeptides by host cell produced enzymes may cause decreased yield of a desired product with correct N-terminal if the N-terminal of the expressed product constitutes a cleavage site for endogenous enzymes. In yeast for example the enzyme Ste13p cleaves at X-Ala or X-Pro, where X can be any amino acid residue. Thus, polypeptides with an Ala or Pro residue as the second residue from the N-terminal end may be cleaved at the N-terminal end and the recovered polypeptide may be a mixture of different degradation products complicating the recovery process and reducing the overall yield.

Furthermore, small polypeptides with little tertiary structure and low content of α-helixes may have a higher tendency to form β-sheets that stack on each other and form fibrils during fermentation and down stream separation and purification steps in large scale production. Formation of fibrils may cause unwanted precipitation with loss of the desired product. Fibrillation may be prevented by treatment at high pH. However, such alkaline treatment is pretty harsh to the product and may cause unwanted formation of D-amino acids residues.

Human GLP-1 is a 37 amino acid residue peptide originating from preproglucagon which is synthesised in the L-cells in the distal ileum, in the pancreas and in the brain. Processing of preproglucagon to give GLP-1$_{(7-36)}$amide, GLP-1$_{(7-37)}$ and GLP-2 occurs mainly in the L-cells. Both GLP-1 and GLP-2 have an Ala as the second amino acid residue from the N-terminal end and are thus prone for N-terminal cleavage when expressed in a host organism such as yeast.

Introduction of lipophilic acyl groups in naturally occurring peptides or analogues thereof has shown to lead to acylated peptides which have a protracted profile relative to the native peptide or unmodified analogues. The present invention provides a method for ensuring preferential acylation at the desired position in the polypeptide in question as it will appear from the following.

SUMMARY OF THE INVENTION

In one aspect the present invention is related to a method for making a polypeptide comprising at least one lysine residue being acylated in its ε-amino group, said method comprising the following steps:
  (i) culturing a host cell comprising a polynucleotide sequence encoding a precursor molecule of the desired polypeptide, said precursor molecule comprising an N-terminal extension capable of protecting the desired polypeptide against proteolytic degradation, said N-terminal extension comprising a cleavage site positioned at its C-terminal end for cleavage from the desired polypeptide, under suitable conditions for expression of said precursor molecule, said cleavage site being not a Lys residue;
  (ii) separating the expressed precursor from the culture broth;
  (iii) acylating the ε-amino group of at least one lysine residue in the desired polypeptide;
  (iv) removing the N-terminal extension by chemical or enzymatic cleavage and
  (v) isolating the acylated polypeptide by suitable means.

DETAILED DESCRIPTION OF THE INVENTION

In one embodiment of the present invention the order of steps (ii) to (iv) may be changed. Thus, in one embodiment of the present invention the acylating step (iii) is conducted after the removal step (iv) so that the N-terminal extension is removed before the polypeptide is acylated in the desired position.

The desired polypeptide may contain more than one lysine residue as a potential target for acylation but will typically only contain one lysine residue. Thus, in one embodiment, the desired polypeptide is monoacylated.

The N-terminal extension will typically be of up to 15 amino acids in length and may be from 1-15; 2-15; 3-15; 3-12; 3-10; 3-9; 3-8; 3-7; 3-6; or 3-5 amino acids in length. The amino acids in the N-terminal extension are selected with a multiple purpose: 1) to protect the expressed precursor molecule against endoproteolytic degradation; 2) to avoid acylation at the N-terminal amino acid residue of the desired polypeptide, i.e. to ensure that acylation takes place preferentially or only at the wanted position in the desired polypeptide; and 3) to prevent precipitation caused by fibrillation during fermentation and down stream processing steps such as separation and purification in large scale production. Furthermore, the amino acid residues at both ends of the N-terminal extension should be selected so as to ensure efficient cleavage of the N-terminal extension from the desired polypeptide at the C-terminal end and at the N-terminal end from possible upstream sequences such as pre- or pre-pro peptides which have the purpose of ensuring transport of the expressed precursor molecule out of the host cell and into the culture medium. Finally, the N-terminal extension may serve as a tag for purification purposes.

The N-terminal extension is found to be stably attached to the precursor molecule of the invention during fermentation, protecting the N-terminal end of the precursor molecule against the proteolytic enzymes such as Ste13p and/or Dap2p.

The N-terminal extension is removably attached to the N-terminal end of the desired polypeptide. Thus, the C-terminal end of the N-terminal extension will constitute a cleavage site or will together with amino acid residues at the N-terminal end of the desired polypeptide constitute a suitable cleavage site. This cleavage site is different from lysine to avoid acylation of the precursor molecule at this position.

Cleavage may be conducted by means of chemicals like cyanogen bromide (E. Gross: Methods in Enzymlogy XI, 1967, 238-255, Editor: C H W Hirs, and J P Whitelegge et al, Protein Science 2000, 9, 1618-1630) or hydroxylamine cleaving at the C-terminal side of Met or Asn. In the case of Asn cleavage is enhanced by the presence of a Gly N-terminal to the cleavage site (Asn ⇓Gly). The cleavage can also be effected by specific exoproteases such as a suitable proteolytic enzyme which is specific for the chosen cleavage site, cleaving at an N-terminal pyroglutamic acid or endoproteases like proline endopeptidases (EC 3.4.22.26) cleaving at the C-terminal side of Pro in polypeptides. Other endoproteases as trypsins cleave at the C-terminal side of many single Arg-residues, while other like Factor Xa is more specific and often cleaves after the sequence Ile-Glu-Gly-Arg. Kex2p or PC1 and similar enzymes cleave at a dibasic cleavage site such as Arg-Arg. A mixture of chemical and enzymatic methods can be used if a Cys residue is placed N-terminally to the polypeptide. The SH-group can easily be acylated with an amine that is generating a pseudo-lysine amino acid which can then be cleaved by *Achromobacter lyticus* protease I after acylation of the lysine residue in the desired polypeptide, thereby protecting this site from cleavage.

In one embodiment, the cleavage site is chosen from the group consisting of Met, Asn, Pro, Gln, Cys and Arg-Arg.

According to one embodiment of the present invention, the desired polypeptide will comprise a Pro, Ala or Ser residue as the second amino acid residue from the N-terminal end. Such polypeptides will be especially vulnerable to degradation by proteolytic enzymes such as Ste13p.

According to a further embodiment, the desired polypeptide will have a His-Ala or a His-Pro, His-Ser or a Tyr as the N-terminal sequence.

In a more specific embodiment, the N-terminal extension has the formula $$X_n\text{------}X_1\text{—}Y$$

wherein $X_n\text{-------}X_1$ is a peptide sequence of from 1-14 amino acid residues in length and Y is Met, Asn, Pro, Gln, Cys or Arg-Arg, the function of $X_n\text{------}X_1\text{—}Y$ being a) to protect the expressed polypeptide from endoproteolytic cleavage, b) to prevent acylation at the N-terminal end of the desired polypeptide and c) to prevent precipitation caused by fibrillation during fermentation and down stream separation and purification steps. The amino acid residues in $X_n\text{------}X_1\text{—}Y$ are furthermore selected to obtain optimal in vitro cleavage of the N-terminal extension at its C-terminal end (at Y) and optimal in vivo cleavage at its N-terminal end (at $X_n$) at a KEX site from upstream signal-leader sequences. The amino acid residues in $X_n\text{------}X_1$ may in principle be any amino acid residue except Lys as long as the peptide sequence fulfils at least one of the required purposes. However, number two amino acid residue from the N-terminal end of the extension is preferably not Ala or Pro.

In one embodiment $X_n\text{------}X_1$ is a peptide sequence of from 1-15; 2-15; 3-15; 3-12; 3-10; 3-9; 3-8; 3-7; 3-6; or 3-5 amino acid residues in length. To ensure efficient cleavage from a pre-pro-sequence at a Kex2 site in a host cell as yeast one or two of the N-terminal amino acid residues in $X_n\text{------}X_1$ are preferably chosen from Glu and Asp. Glu and/or Asp positioned at the N-terminal end of the N-terminal extension will also protect the expressed molecule against proteolytic degradation in the yeast cell.

Examples of N-terminal extensions are Glu-Glu-Met; Glu-Glu-Ala-Glu-Met(SEQ ID NO:1); Glu-Glu-Ala-Glu-Asn (SEQ ID NO:2); Glu-Glu-Ala-Glu-Arg-Arg(SEQ ID NO:3); Gln; Glu-Pro-Gln(SEQ ID NO:4); Glu-Ala-Gln; Glu-Ala-Glu-Ala-Gln(SEQ ID NO:5); Glu-Ala-Glu-Ala-Glu-Ala-Gln (SEQ ID NO:6); Glu-Glu-Gly-Cys-Thr-Ser-Ile-Cys(SEQ ID NO:7); Glu-His-Gly-Cys-Thr-Ser-Ile-Cys(SEQ ID NO:8); Glu-Glu-Ala-Arg-Met(SEQ ID NO:9); Glu-Glu-Arg-Asn (SEQ ID NO:10); Glu-Glu-Ala-Glu-Asn(SEQ ID NO:11); Glu-Glu-Arg-Ala-Arg-Arg(SEQ ID NO:12); Glu-Glu-Ala-Glu-Pro(SEQ ID NO:13); Glu-Glu-Gly-Glu-Pro(SEQ ID NO:14); Glu-Glu-Ala-Glu-Cys(SEQ ID NO:15) and Glu-Glu-Ile-Glu-Gly-Arg(SEQ ID NO:16).

According to a further aspect the present invention is related to a polypeptide precursor for a desired polypeptide said polypeptide precursor having the formula N-terminal extension-$Y_1$-*polypeptide* wherein $Y_1$ is Met, Asn, Pro, Gln, Cys or Arg-Arg; the N-terminal extension has 1-14 amino acid residues as described above and *polypeptide* is the remaining part of the desired polypeptide.

According to a still further aspect the present invention is related to a polypeptide precursor for a desired polypeptide said polypeptide precursor having the formula N-terminal extension-$Y_1$—$Y_2$—$Y_3$-*polypeptide* wherein $Y_1$ is Met, Asn, Pro, Gln, Cys or Arg-Arg; $Y_2$ is His or Tyr, $Y_3$ is Ala, Ser or Gly, the N-terminal extension has. 1-14 amino acid residues as described above and *polypeptide* is the remaining part of desired polypeptide.

More specifically, $Y_2$ is N-terminal amino acid residue in the desired polypeptide and $Y_3$ is the second amino acid residue from the N-terminal end of the desired polypeptide According to further aspects the present invention is related to polynucleotides encoding the claimed polypeptide precursors and vectors and transformed host cells containing such polynucleotides.

Introduction of lipophilic acyl groups in naturally occurring peptides or analogues thereof has shown to lead to acylated peptides which have a protracted profile relative to the native peptide or unmodified analogues. This phenomenon is disclosed and demonstrated in WO 98/08871 which discloses acylation of GLP-1 and analogues thereof and in WO 98/08872 which discloses acylation of GLP-2 and analogues thereof. The lipophilic group may be introduced by means of mono- or dipeptide spacers as disclosed in WO 98/08871. Alternatively, the lipophilic group may be introduced by means of α-amino-α,ω-dicarboxylic acid groups as disclosed in WO 00/55119.

The present polypeptide precursor will contain at least one lysine group with a free ε-amino group to be acylated. When acylating one or more free amino acid groups in a polypeptide acylation of the free amino group in the N-terminal amino acid residue is more or less avoidable. Certain methods have been developed to avoid acylation at the N-terminal amino acid residue, vide U.S. Pat. No. 5,905,140. The present invention offers an alternative solution to the problem, i.e. to express an N-terminally extended precursor of the desired polypeptide. So even if acylation takes place both at the desired position in the desired polypeptide and at the N-terminal amino acid residue, subsequent cleavage of the N-terminal extension from the desired polypeptide will removed the unwanted acylated amino acid residue. The precursor molecule can thus be preferentially acylated in the desired lysine residue which in the case of GLP-1 is the lysine in position 26. After acylation the acylated precursor molecule is cleaved by suitable chemical or enzymatic means as described above and the desired acylated polypeptide can be isolated.

The acylation step (iii) may be conducted at a pH between 7 and 12. In certain embodiments, the pH will be between 8 and 11.5 or between 9.0 and 10.5 and a pH value of about 9.5 to 10.5 has proven to be efficient. The temperature will be between minus 5 and 35° C. and will typically be between 0 and 20° C. or between 15 and 30° C.

Definitions

The term "preferential acylating" is meant to include and acylation process where acylation takes place at one or more preferred positions in the molecule in a higher degree than at other positions in the same molecule. Thus, the acylation at the preferred positions is preferably at least 50, more preferred at least 80 and most preferred 90-100% of the total acylation.

With "N-terminal extension" is meant a polypeptide sequence removably attached to the N-terminal amino acid residue in the desired polypeptide. The N-terminal extension may be 1-15 amino acid residues in length and will not comprise a Lys residue. The N-terminal extension will protect the expressed fusion polypeptide against proteolytic degradation within the host cell as described above.

With "desired polypeptide" is meant the ultimate polypeptide obtained after cleavage of the N-terminal extension from the precursor molecule. This expression will cover both the acylated and non-acylated version of said polypeptide. The "N-terminal extension" includes the cleavage site for cleavage of the N-terminal extension from the desired polypeptide's N-terminal end. It will be understood that whenever a specific N-terminal extension or a sequence being comprised in the N-terminal extension is shown, then the given C-terminal amino acid residue will be the cleavage site directly linked to the N-terminal amino acid residue of the desired polypeptide.

An example of a desired polypeptide is GLP-1. The amino acid sequence of GLP-1 is given i.a. by Schmidt et al. (*Diabetologia* 28 704-707 (1985). Although the interesting pharmacological properties of GLP-1(7-37) and analogues thereof have attracted much attention in recent years only little is known about the structure of these molecules. The secondary structure of GLP-1 in micelles has been described by Thornton et al. (*Biochemistry* 33 3532-3539 (1994)), but in normal solution,GLP-1 is considered a very flexible molecule.

A simple system is used to describe fragments and analogues of this peptide. Thus, for example, $Gly^8GLP\text{-}1_{(7-37)}$ designates a fragment of GLP-1 derived from $GLP\text{-}1_{(1-37)}$ by deleting the amino acid residues Nos. 1 to 6 and substituting the naturally occurring amino acid residue in position 8 (Ala) by Gly. Similarly, $Lys^{26}(N^\epsilon\text{-tetradecanoyl})\text{-}GLP\text{-}1_{(7-37)}$ designates $GLP\text{-}1_{(7-37)}$ wherein the ε-amino group of the Lys residue in position 26 has been tetradecanoylated.

Other examples of a desired polypeptides are GLP-2 and glucagon both belonging to the GRF (growth hormone releasing factor) family of peptides having a His or Tyr in the N-terminal position and Ser, Ala or Gly in the next position, vide Adelhorts K. et al., The Journal of Biological Chemistry (1994) p 6275-6278).

"POT" is the *Schizosaccharomyces pombe* triose phosphate isomerase gene, and "TPI1" is the *S. cerevisiae* triose phosphate isomerase gene.

With "fibrillation" is meant a process where so called "fibrils" are formed. "Fibrils" is a well recognized and described phenomenon and may be composed of antiparallel β-sheets. Molecules like GLP's with little α-helical structure and a very flexible and little tertiary structure are very prone to aggregation that leads to precipitation and loss of yield if very crude chemical conditions are not taken in use such as alkaline treatment at pH ~12.

By a "leader" is meant an amino acid sequence consisting of a pre-peptide (the signal peptide) and a pro-peptide.

The term "signal peptide" is understood to mean a pre-peptide which is present as an N-terminal sequence on the precursor form of a protein. The function of the signal peptide is to allow the heterologous protein to facilitate translocation into the endoplasmic reticulum. The signal peptide is normally cleaved off in the course of this process. The signal peptide may be heterologous or homologous to the yeast organism producing the protein. A number of signal peptides may be used with the DNA construct of the invention including the YP1 signal peptide (formally called the YAP3 signal peptide) or any functional analogue thereof (Egel-Mitani et al. (1990) YEAST 6:127-137 and U.S. Pat. No. 5,726,038) and the α-factor signal of the MFα1 gene (Thorner (1981) in *The Molecular Biology of the Yeast Saccharomyces cerevisiae*, Strathern et al., eds., pp 143-180, Cold Spring Harbor Laboratory, NY and U.S. Pat. No. 4,870,00.

The term "pro-peptide" means a polypeptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The pro-peptide may be the yeast α-factor pro-peptide, vide U.S. Pat. Nos. 4,546,082 and 4,870,008. Alternatively, the pro-peptide may be a synthetic pro-peptide, which is to say a pro-peptide not found in nature. Suitable synthetic pro-peptides are those disclosed in U.S. Pat. Nos. 5,395,922; 5,795,746; 5,162,498 and WO 98/32867. The pro-peptide will preferably contain an endopeptidase processing site at the C-terminal end, such as a Lys-Arg sequence or any functional analog thereof.

The polynucleotide sequence of the invention may be prepared synthetically by established standard methods, e.g. the phosphoamidite method described by Beaucage et al. (1981) Tetrahedron Letters 22:1859-1869, or the method described by Matthes et al. (1984) EMBO Journal 3:801-805. According to the phosphoamidite method, oligonucleotides are synthesized, for example, in an automatic DNA synthesizer, purified, duplexed and ligated to form the synthetic DNA construct. A currently preferred way of preparing the DNA construct is by polymerase chain reaction (PCR).

The polynucleotide sequence of the invention may also be of mixed genomic, cDNA, and synthetic origin. For example, a genomic or cDNA sequence encoding a leader peptide may be joined to a genomic or cDNA sequence encoding the precursor molecule of the invention, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The invention encompasses a vector which is capable of replicating in the selected microorganism or host cell and which carries a polynucleotide sequence encoding the precursor molecule of the invention. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

In a preferred embodiment, the recombinant expression vector is capable of replicating in yeast. Examples of sequences which enable the vector to replicate in yeast are the yeast plasmid 2 µm replication genes REP 1-3 and origin of replication.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (ornithine carbamoyl-transferase), pyrG (orotidine-5'-phosphate decarboxylase) and trpC (anthranilate synthase. Suitable markers for yeast host cells are ADE2, HIS3, LEU2, LYS2, MET3, TRP1, and URA3. A preferred selectable marker for yeast is the *Schizosaccharomyces pompe* TPI gene (Russell (1985) Gene 40:125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the Saccharomyces cerevisiae MFα1, TPI, ADHm Gal or PGK promoters.

The polynucleotide construct of the invention will also typically be operably connected to a suitable terminator. In yeast a suitable terminator is the TPI terminator (Alber et al. (1982) J. Mol. Appl. Genet. 1:419-434) or the CYC1 terminator.

The procedures used to ligate the polynucleotide sequence of the invention, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the precursor molecule of the invention, and subsequently inserting this fragment into a suitable expression vector, or by sequentially inserting DNA fragments containing genetic information for the individual elements followed by ligation.

The present invention also relates to recombinant host cells, comprising a polynucleotide sequence encoding the precursor molecule of the invention. A vector comprising such polynucleotide sequence is introduced into the host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The host cell may be a prokaryote or a eukaryote cell. Useful prokaryotes are bacterial cells such as gram positive bacteria including *Bacillus* and *Streptomyces* cells, or gram negative bacteria such as *E. coli* and *Pseudomonas* sp. Cells. Eukaryote cells may be mammalian, insect, plant, or fungal cells. In a one embodiment, the host cell is a yeast cell. The yeast organism used in the process of the invention may be any suitable yeast organism which, on cultivation, produces large amounts of the precursor molecule. Examples of suitable yeast organisms are strains selected from the yeast species *Saccharomyces cerevisiae, Saccharomyces kluyveri, Schizosaccharomyces pombe, Sacchoromyces uvarum, KJuyveromyces lactis, Hansenula polymorpha, Pichia pastoris, Pichia methanolica, Pichia kluyveri, Yarrowia lipolytica, Candida sp., Candida utilis, Candida cacaoi, Geotrichum sp.,* and *Geotrichum fermentans.*

The transformation of the yeast cells may for instance be effected by protoplast formation followed by transformation in a manner known per se. The medium used to cultivate the cells may be any conventional medium suitable for growing yeast organisms. The secreted precursor of the invention may then be recovered from the medium by conventional procedures including separating the yeast cells from the medium by centrifugation, filtration or catching the precursor by an ion exchange matrix or by a reverse phase absorption matrix, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

In the present text, the designation "an analogue" is used to designate a peptide wherein one or more amino acid residues of the parent peptide have been substituted by another amino acid residue and/or wherein one or more amino acid residues of the parent peptide have been deleted and/or wherein one or more amino acid residues have been added to the parent peptide. Such addition can take place either at the N-terminal end or at the C-terminal end of the parent peptide or both.

The term "derivative" is used in the present text to designate a peptide in which one or more of the amino acid residues of the parent peptide have been chemically modified, e.g. by alkylation, acylation, ester formation or amide formation.

EXAMPLES

Example 1

Expression of N-Terminally Extended $Arg^{34}GLP-1_{(7-37)}$

The host strain ME1719 is a diploid strain and has a phenotype which lacks two aspartyl protease activities, i.e. YPS1 (previously called YAP3) which cleaves C-terminal side of mono- or dibasic amino acid residues (Egel-Mitani, et al., YEAST 6: 127-137, 1990) and PEP4 a vacuolar protease A responsible for activation of other proteases such as protease B, carboxypeptidase Y, aminopeptidase I , RNase, alkaline phosphatase, acid threhalase and exopolyphosphatase. Moreover the triose phosphate isomerase gene (TPI) has been disrupted which phenotype makes it possible to utilize glucose in transformants grown on glucose containing medium. The genetic background of ME1719 is MATa/αΔyps1::ura3/Δyps1::URA3 pep4-3/pep4-3 Δtpi::LEU2/Δtpi::LEU2 leu2/leu2 Δura3/Δura3.

Figure 1:
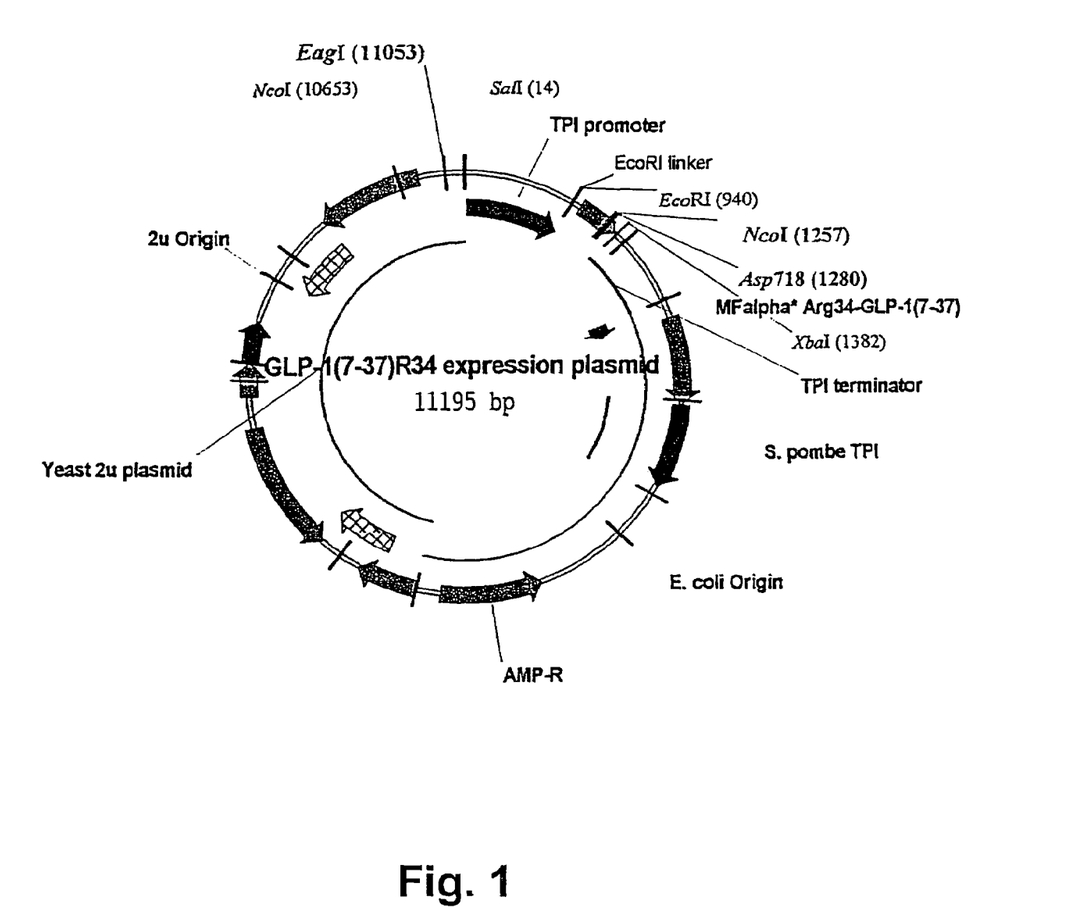
FIG. 1 shows the plasmid pKV304 which contain DNA encoding $Arg^{34}GLP-1_{(1-37)}$ under regulatory control of the TPI promoter and -terminator and the MFalpha prepro sequence. This plasmid is the starting plasmid for making expression plasmids for the precursor molecules according to the present invention.

Expression plasmids containing the N-terminally extended $Arg^{34}GLP-1_{(1-37)}$ were made as follows: Plasmid pKV304 containing DNA encoding $Arg^{34}GLP-1_{(7-37)}$ without an N-terminal extension was digested with either EagI+NcoI or EagI+Asp718. After agarose electrophoresis and GeneClean™ III purification, fragments of 1.4 kb and 10 kb, respectively were isolated. Oligonucleotide adaptors corresponding to various N-terminal extensions of $Arg^{34}$ $GLP-1_{(7-37)}$ containing NcoI and Asp718 cleavage sites were likewise purified as described above. The 1.4 kb fragment (EagI+NcoI), 10 kb fragment (EagI+Asp718) and the adaptor fragment designed for the N-terminal extension of $Arg^{34}GLP-1_{(7-37)}$ (NcoI+Asp718) were ligated and transformed in *E. coli* strain MT172 and plasmid DNA was sequenced to verify the correct N-terminally extended $Arg^{34}GLP-1_{(7-37)}$.

Plasmid DNA was then transformed into yeast strain ME1719 and yeast transformants were isolated twice on MUPD selective plates. Yeast cells were cultured in 5 ml MUPD medium for 3 days at 30° C. and culture supernatants were analyzed by HPLC and MALDI-MS (Matrix Assisted Laser Desorption/Inonisation Mass Spectrometry).

Table 1 shows the different GLP-1 precursors and the yield compared to a control with no N-terminal extension.

TABLE 1

| Extension | Polypeptide | Yield Percentage of control |
|---|---|---|
| None (control) | $Arg^{34}GLP-1_{(7-37)}$ | 100 |
| EEM | $Arg^{34}GLP-1_{(7-37)}$ | 199 |
| EEAEM, SEQ ID NO: 1 | $Arg^{34}GLP-1_{(7-37)}$ | 247 |
| EEAEN, SEQ ID NO: 2 | $Arg^{34}GLP-1_{(7-37)}$ | 249 |
| EEAERR, SEQ ID NO: 3 | $Arg^{34}GLP-1_{(7-37)}$ | 159 |
| EERARR, SEQ ID NO: 12 | $Arg^{34}GLP-1_{(7-37)}$ | 40 |
| Q | $Arg^{34}GLP-1_{(7-37)}$ | 107 |
| EPQ | $Arg^{34}GLP-1_{(7-37)}$ | 232 |
| EAQ | $Arg^{34}GLP-1_{(7-37)}$ | 146 |
| EAEAQ, SEQ ID NO: 5 | $Arg^{34}GLP-1_{(7-37)}$ | 227 |
| EAEAEAQ, SEQ ID NO: 6 | $Arg^{34}GLP-1_{(7-37)}$ | 251 |
| EEAEP, SEQ ID NO: 13 | $Arg^{34}GLP-1_{(7-37)}$ | 229 |
| EEGEP, SEQ ID NO: 14 | $Arg^{34}GLP-1_{(7-37)}$ | 171 |
| EEGCTSIC, SEQ ID NO: 7 | $Arg^{34}GLP-1_{(7-37)}$ | 68 |
| EHGCTSIC, SEQ ID NO: 8 | $Arg^{34}GLP-1_{(7-37)}$ | 31 |
| EEAEC SEQ ID NO: 15 | $Arg^{34}GLP-1_{(7-37)}$ | 89, 76* |
| EEIEGR, SEQ ID NO: 16 | $Arg^{34}GLP-1_{(7-37)}$ | 166 |

*Two peaks

Acylation of the isolated precursor molecules is conducted according to the methods described in WO 98/08871, WO 98/09972, WO 00/55119 or U.S. Pat. No. 5,905,140. Cleavage of the N-terminal extension from the desired molecule will depend on which cleavage site has been chosen and will then follow standard procedures.

Example 2

Cleavage of Glu-Glu-Ala-Glu-Asn(SEQ ID NO:2)-$Arg^{34}GLP-1_{(7-37)}$ by hydroxylamine Inclusion of asparagine N-terminally to the N-terminal His residue (His-7) in GLP-1 might open the possibility of cleaving selectively with hydroxylamine, as no other Asn is present in the GLP17-37, R34 amino acid sequence. Preferential cleavage at Asn-Gly motifs is well established in protein technology (Bornstein, P. and Balian, G. (1970) *J. Biol. Chem.* 245, 4854-4856 and Blodgett, J. K., Loudon, G. M., and Collins, K. D. (1985) *J. Am. Chem. Soc.* 107, 4305-4313). It has been shown that the willingness of Asn-Xxx cleavage roughly follows the spatial availability, i.e small Xxx residues are prefered (Geiger, T. and Clarke, S. (1987) *J. Biol. Chem.* 262, 785-794). According to the present invention it has surprisingly been demonstrated that the motive Asn-His constitutes a cleavage site when only one Asn is present. Potential problems with the hydroxylamine method might be cleavages at Asp-15 or Glu-9/Glu-21/Glu-27. However, Asp and Glu residues are typically much less reactive towards hydroxylamine and imid formation (compared to Asn). Racemization of His-7 during the process might be a concern, but given the mild applied conditions, this is most likely not taking place.

Glu-Glu-Ala-Glu-Asn(SEQ ID NO:2)-GLP-1 was expressed in yeast and purified as previously described. Afterwards the peptide was acylated by use of Nε-palmitoyl-Glu-γ-succinimidyl-α-tert-butyl ester and deprotected by use of TFA. Reverse-phase HPLC-MS identified the desired product, Glu-Glu-Ala-Glu-Asn(SEQ ID NO:2)-NN2211 acylated in position Lys-26 in a yield of 80%. 20% of the acylation mixture was acylated both in Lys-26 and N-terminally. Since cleavage of both these peptides at Asn-His should yield the same product Arg$^{34}$GLP-1$_{(7-37)}$ it was decided to do the exploratory studies with the 80/20 mixture.

Screening of cleavage conditions was performed as follows:

| Time/hours | 2 | 4 | 20 | |
|---|---|---|---|---|
| Temperature/° C. | 45 | 65 | 85 | |
| pH | 7 | 8 | 9 | |
| Conc., NH$_2$OH/M | 0.5 | 1 | 3 | 5 |

Optimal conditions in the screened ranges were found to be 20 hours, 45° C., pH 7, 3-5 M hydroxylamine with cleavage yields of 80-90% as judged from HPLC. Shorter times or lower hydroxylamine concentrations gave incomplete cleavages. Higher temperatures or higher pH's gave increasing levels of side-products.

Example 3

Cleavage of Non-Acylated Glu-Glu-Ile-Glu-Gly-Arg(SEQ ID NO:16)-Arg$^{34}$GLP-1$_{(7-37)}$ with FXa Glu-Glu-Ile-Glu-Gly-Arg(SEQ ID NO:16)-Arg$^{34}$GLP-1$_{(7-37)}$ was expressed and recovered as previously described. 1 mg lyophilized product was dissolved in 10 ml 0.02 M Tris and 2 mM CaCl$_2$, pH 7.5. At time zero 40 units of FXa (Amersham Pharmacia Biotech, Product number: 27-0849-01) was added and the incubation was stopped after 2 hours at 30° C. in a water bath by dilution 1:1 with 1 M HAc. Determination by HPLC and MALDI-TOF showed 82% correctly cleaved Arg$^{34}$GLP-1$_{(7-37)}$ and 18% non-cleaved product Glu-Glu-Ile-Glu-Gly-Arg(SEQ ID NO:16)-Arg$^{34}$GLP-1$_{(7-37)}$. Arg$^{34}$GLP-1$_{(7-37)}$ can then be acylated by well established known methods.

Example 4

Cleavage of Non-Acylated Glu-Glu-Ala-Glu-Arg-Arg(SEQ ID NO:3)-Arg$^{34}$GLP-1$_{(7-37)}$ with kexin Glu-Glu-Ala-Glu-Arg-Arg(SEQ ID NO:3)-Arg$^{34}$GLP-1$_{(7-37)}$ was expressed and recovered as previously described. 0.37 mg lyophilized product was dissolved in 900 µl 0.1 M NaAc and 5 mM CaCl$_2$, pH 6.0. At time zero 100 µl of soluble C-terminal truncated kexin was added and the mixture was incubated in a water bath at 30° C. After 1 hour the reaction was stopped by addition of 2 M HAc 1:1 and cleavage was determined by HPLC and MALDI-MS. 66.9% was cleaved to Arg$^{34}$GLP-1$_{(7-37)}$ and the rest was uncleaved Glu-Glu-Ala-Glu-Arg-Arg(SEQ ID NO:3)-Arg$^{34}$GLP-1$_{(7-37)}$. Arg$^{34}$GLP-1$_{(7-37)}$ can then be acylated by well established known methods.

Example 5

Cleavage of Non-Acylated Glu-Glu-Ala-Glu-Pro(SEQ ID NO:13)-Arg$^{34}$GLP-1$_{(7-37)}$ with prolylendopeptidase Glu-Glu-Ala-Glu-Pro(SEQ ID NO:13)-Arg$^{34}$GLP-1$_{(7-37)}$ was expressed and recovered as previously described. 11.4 mg lyophilized product was dissolved in 50 ml 0.02 M Tris, HCl, pH 7.5. At time zero 500 µl was added of prolylendopeptidase (*Sphingomonas capsulata* prolylendopeptidase expressed in *E. coli* according to Kanatani et al, Archives of Biochemistry and Biophysics, 358, 141-148 (1998). Cleavage and formation of Arg$^{34}$GLP-1$_{(7-37)}$ are detected after 30 min incubation in a water bath at 30° C. Arg$^{34}$GLP-1$_{(7-37)}$ can now be acylated by well established, known methods.

What is claimed is:

1. A method for making GLP-1 or a GLP-1 analogue comprising at least one lysine residue being acylated in its ε-amino group, said method comprising the following steps:
   (i) culturing a host cell comprising a polynucleotide sequence encoding a precursor molecule of the GLP-1 or GLP-1 analogue under suitable conditions for expression of the precursor molecule said precursor molecule comprising an N-terminal extension capable of protecting the GLP-1 or GLP-1 analogue against proteolytic degradation, said N-terminal extension comprising: i) a sequence of Glu-Glu-Ala-Glu(SEQ ID NO:27), and ii) a cleavage site positioned at its C-terminal end for cleavage from the GLP-1 or GLP-1 analogue, wherein the cleavage site is not a Lys;
   (ii) separating the expressed precursor from the culture broth;
   (iii) acylating the ε-amino group of at least one lysine residue in the desired polypeptide;
   (iv) removing the N-terminal extension by chemical and/or enzymatic cleavage and isolating the acylated polypeptide by suitable means,
   wherein said GLP-1 or GLP-1 analogue is a peptide of GLP-1(7-36) or GLP-1(7-37).

2. A method according to claim 1, wherein the polypeptide is monoacylated.

3. A method according to claim 1, wherein the polypeptide is $Arg^{34}GLP1_{(7-37)}$ acylated in position $Lys^{26}$.

4. A method according to claim 1, wherein the N-terminal extension is selected from the group consisting of Glu-Glu-Ala-Glu-Met(SEQ ID NO: 1); Glu-Glu-Ala-Glu-Asn(SEQ ID NO:2); Glu-Glu-Ala-Glu-Arg-Arg(SEQ ID NO:3); Glu-Glu-Ala-Glu-Asn(SEQ ID NO:11); Glu-Glu-Ala-Glu-Pro (SEQ ID NO:13); and Glu-Glu-Ala-Glu-Cys(SEQ ID NO:15).

5. A method according to claim 1, wherein the host cell is a yeast cell.

6. A method according to claim 5, wherein the yeast cell is a *Saccharomyces cerevisiae* cell.

* * * * *

UNITED STATES PATENT AND TRADEMARK OFFICE
CERTIFICATE OF CORRECTION

PATENT NO. : 7,572,884 B2 Page 1 of 1
APPLICATION NO. : 11/191574
DATED : August 11, 2009
INVENTOR(S) : Hoeg-Jensen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 306 days.

Signed and Sealed this

Seventh Day of September, 2010

David J. Kappos
*Director of the United States Patent and Trademark Office*